(12) United States Patent
Weinand et al.

(10) Patent No.: US 12,006,549 B2
(45) Date of Patent: Jun. 11, 2024

(54) METHODS UTILIZING LEUKOCYTE RNA EXPRESSION IN PROGNOSIS EVALUATION OF MEDICAL INTERVENTIONS FOR EPILEPSY

(71) Applicant: Arizona Board of Regents on behalf of the University of Arizona, Tucson, AZ (US)

(72) Inventors: Martin E. Weinand, Tucson, AZ (US); Ryan Sprissler, Tucson, AZ (US); Michael F. Hammer, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 456 days.

(21) Appl. No.: 17/269,092

(22) PCT Filed: Oct. 4, 2019

(86) PCT No.: PCT/US2019/054733
§ 371 (c)(1),
(2) Date: Feb. 17, 2021

(87) PCT Pub. No.: WO2020/072926
PCT Pub. Date: Apr. 9, 2020

(65) Prior Publication Data
US 2021/0246509 A1    Aug. 12, 2021

Related U.S. Application Data

(60) Provisional application No. 62/741,719, filed on Oct. 5, 2018.

(51) Int. Cl.
| | | |
|---|---|---|
| *C12Q 1/68* | (2018.01) | |
| *C12Q 1/686* | (2018.01) | |
| *C12Q 1/6883* | (2018.01) | |
| *A61N 7/00* | (2006.01) | |

(52) U.S. Cl.
CPC .......... *C12Q 1/6883* (2013.01); *C12Q 1/686* (2013.01); *A61N 7/00* (2013.01); *C12Q 2600/158* (2013.01); *G01N 2800/2857* (2013.01); *G01N 2800/52* (2013.01)

(58) Field of Classification Search
None
See application file for complete search history.

(56) References Cited

PUBLICATIONS

Dixit et al; Genomics, vol. 107, 2016, pp. 178-188.*

* cited by examiner

*Primary Examiner* — Jehanne S Sitton
(74) *Attorney, Agent, or Firm* — Quarles & Brady LLP; Stephanie Vavra; Yakov S. Sidorin

(57) ABSTRACT

Methods involving analysis of pretreatment leukocyte expression profiles for prognostic assessment of seizure outcome following a treatment or medical procedure, such as stereotactic laser amygdalohippocampotomy (SLAH). In one aspect, RNA sequencing (RNA-Seq) on whole blood leukocyte samples is taken from a patient with intractable epilepsy prior to SLAH. Differential expression (DE) analysis revealed 24 significantly dysregulated genes (≥2.0-fold change, p-value <0.05, and False Discovery Rate, FDR <0.05) useful in prognostic assessment.

4 Claims, 5 Drawing Sheets

METHODS UTILIZING LEUKOCYTE RNA EXPRESSION IN PROGNOSIS EVALUATION OF MEDICAL INTERVENTIONS FOR EPILEPSY

CROSS-REFERENCE TO RELATED APPLICATIONS

This patent application represents the national stage entry of PCT International Application No. PCT/US2019/054733 filed Oct. 4, 2019, which claims priority from and benefit of the U.S. Provisional Patent Application No. 62/741,719 filed on Oct. 5, 2018, and entitled "Methods Utilizing Leukocyte RNA Expression in Prognostic Evaluation of Medical Interventions for Epilepsy". The disclosure of each of the above-identified patent applications the entirety of which is hereby incorporated herein by reference in its entirety herein.

STATEMENT REGARDING FEDERALLY SPONSORED RESEARCH OR DEVELOPMENT

This invention was made with government support under Grant No. R01 MH065151, awarded by the National Institutes of Health. The government has certain rights in the invention.

BACKGROUND

The prevalence of epilepsy in the United States is approximately 1% [1]. Among patients with epilepsy, approximately 30% are defined as medically intractable and are potential candidates for epilepsy surgery [2]. The most commonly performed surgical procedure for intractable epilepsy is craniotomy for amygdalohippocampectomy (AH) with or without anterior temporal lobectomy [3,4]. Recently, stereotactic laser amygdalohippocampotomy (SLAH) has been developed as a minimally invasive procedure for treatment of intractable temporal lobe epilepsy (TLE) [5]. Post-operative seizure freedom rates in AH and SLAH are ~65% and ~54%, respectively, with seizure persisting in the remaining patients [4,5]. Therefore, selection criteria for surgical candidates with improved prognostic value for post-operative seizure-free outcome would be of great value [6].

SUMMARY

In some embodiments, a method of processing a RNA-containing sample from a subject with intractable epilepsy is disclosed. Such a method includes the steps of processing an RNA-containing sample from a subject with intractable epilepsy with a machine-based analytical platform to detect a level of 24 genes, wherein the genes comprises FAM155A, ABCA4, ZFP57, IFI27, C5orf17, PLP1, PVRL2, FAM118A, GFAP, CDYL, CPEB4, FADS2, RSAD2, BIN3, BRSK1, AKAP7, IL22RA1, BGN, MMP8, PF4VI, MDGA1, ALOX15B, HBG1, and B4GALNT3.

In the above mentioned and other embodiments, the analytical platform may comprise any known to detect levels of a gene product in a sample, e.g., one or more of quantitative real time PCR and digital droplet PCR.

In other embodiments, a method of selecting a treatment for a subject with intractable epilepsy is described. The method includes the steps of processing an RNA-containing sample from a subject with intractable epilepsy with a machine-based analytical platform to detect a level of 24 genes, wherein the genes comprise FAM155A, ABCA4, ZFP57, IFI27, C5orf17, PLP1, PVRL2, FAM118A, GFAP, CDYL, CPEB4, FADS2, RSAD2, BIN3, BRSK1, AKAP7, IL22RA1, BGN, MMP8, PF4VI, MDGA1, ALOX15B, HBG1, and B4BALNT3; and selecting an ablation treatment if FAM155A, ABCA4, ZFP57, IFI27, C5orf17, PLP1, PVRL2, FAM118A, GFAP, CDYL, CPEB4, FADS2, RSAD2, BIN3, BRSK1, and AKAP7 are upregulated and IL22RA1, BGN, MMP8, PF4VI, MDGA1, ALOX15B, HBG1, and B4GALNT3 are downregulated relative to a control expression level for each gene.

The ablation treatment for embodiments herein may include stereotactic laser amygdalohippocampotomy (SLAH) ablation of the amygdala and hippocampus, from the amygdala anteriorly to the hippocampus at least at the level of the tectum posteriorly. Other surgical and non-surgical (e.g., MRI-guided focused ultrasound ablation or focused ultrasound ablation) treatments may be used that accomplish the same result.

Further embodiments involve the use of a panel of genes to predict a seizure free outcome following an ablation treatment for a subject with intractable epilepsy, wherein the panel includes FAM155A, ABCA4, ZFP57, IFI27, C5orf17, PLP1, PVRL2, FAM118A, GFAP, CDYL, CPEB4, FADS2, RSAD2, BIN3, BRSK1, AKAP7, IL22RA1, BGN, MMP8, PF4VI, MDGA1, ALOX15B, HBG1, and B4GALNT3.

BRIEF DESCRIPTION OF DRAWINGS

The technology disclosed herein will be better understood from a reading of the following detailed description taken in conjunction with the drawings in which like reference designators are used to designate like elements, and in which.

DETAILED DESCRIPTION

Figure 1:
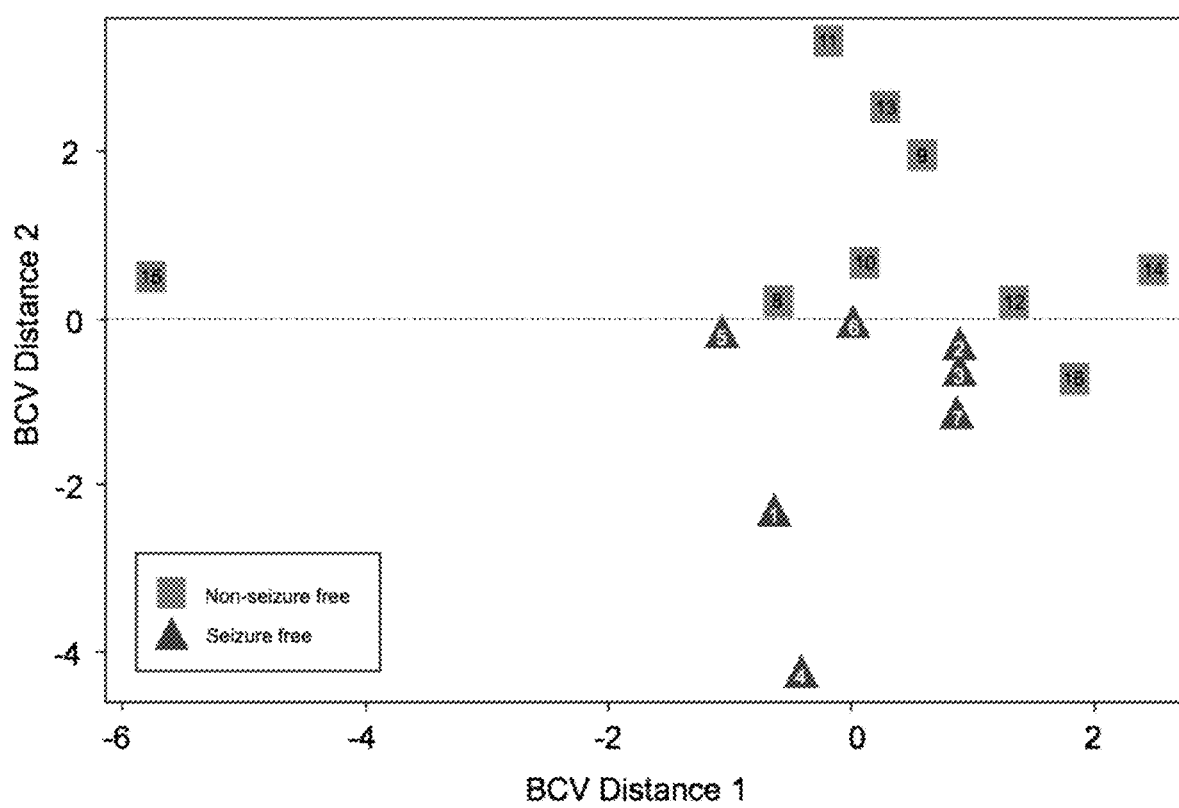
FIG. 1 depicts a multidimensional scaling plot (MDS) generated using edgeR showing segregation of non-seizure free patients vs seizure free patients PBMC transcriptional profile following SLAH. All annotated transcripts for all samples were used to generate plot. Numbered sample IDs indicate patient from list in Table 1 (see Detailed Description). BCV=Biological Coefficient of Variance.

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

Traditional selection criteria for epilepsy surgery candidates have included seizure focus localization using non-invasive and invasive long-term ictal EEG recording, MRI brain and positron emission tomography brain scanning, and neuropsychological testing [7]. Yet another strategy for the selection of patients for surgery involves the identification of biomarkers to predict surgical outcome.

Among other embodiments, disclosed herein is an approach known as "neurosurgical genomics", in which RNA-Seq is employed to identify gene expression profiles in patients with different seizure outcome after SLAH [8,9].

Previous genetic profiling studies on resected tissue utilizing microarray technology identified temporal cortical and hippocampal RNA expression patterns that differed between patients with SF and NSF outcome following anterior temporal lobectomy with AH [8,9]. Given the bidirectional cellular and molecular interactions between leukocytes and the epileptic brain, systemic (peripheral) leukocytes may offer a relatively noninvasive means to assess differences in gene expression that are induced under conditions recapitulating or reflecting temporal lobe epilepsy pathophysiology. Many of these interactions involve immunosurveillance trafficking by leukocytes within epileptic brain tissue and the delivery of brain macromolecules, solutes, and immune cells to cervical lymph nodes where T-cell modulation occurs. These multimodal leukocyte/brain communications offer an opportunity to detect altered leukocyte expression profiles by virtue of the fact that leukocytes are able to access cortical tissue and flow back out to the peripheral blood. On this basis, it was hypothesized that pre-operative peripheral leukocyte RNA expression parameters have prognostic value for post-operative seizure-free outcome.

In one embodiment, the identification of a panel of such biomarkers could be used to improve patient selection for neurosurgical operative intervention or another intervention, such as an MRI-guided focused ultrasound or a focused ultrasound-based intervention that would have similar results to surgery but not involve an incision or other invasive aspect. Our differential expression data were obtained through the use of RNA-Seq, a next generation sequencing (NGS) method with improved sensitivity and dynamic range compared with microarray-based profiling (REFS). Based on our results, systemic leukocyte gene expression serves as a prognostic biomarker for successful outcome from operative neurosurgical intervention [10].

Examples

Clinical Demographics. A total of 16 consecutive patients (mean age: 39.4 years, range: 16-62 years; 10 males, 6 females) underwent comprehensive evaluation for epilepsy surgery candidacy. In this series, seven patients were rendered seizure-free and nine patients were not seizure-free following SLAH (Table 1).

TABLE 1

Patient Clinical Demographics for Stereotactic Laser Amygdalohippocampotomy (SLAH) Series

| Sample# | Gender | Age (yrs) | BSF (sz/mo) | Etiology | Outcome | Duration (yrs) | Follow-up (mos) | Laterality |
|---|---|---|---|---|---|---|---|---|
| 1 | M | 38 | 3 | Unk | SF | 17 | 16 | R |
| 2 | M | 37 | 0.25 | Unk | SF | 35 | 15 | L |
| 3 | M | 60 | 0.25 | Unk | SF | 47 | 13 | L |
| 4 | M | 26 | 1 | Unk | SF | 4 | 13 | R |
| 5 | F | 32 | 0.33 | CVA | SF | 8 | 32 | R |
| 6 | M | 16 | 4 | Unk | SF | 10 | 12 | R |
| 7 | F | 35 | 1 | Unk | SF | 13 | 17 | R |
| 8 | F | 54 | 1 | Pre | NSF | 36 | 13 | L |
| 9 | F | 45 | 4 | Abor | NSF | 8 | 14 | R |
| 10 | M | 46 | 2 | Unk | NSF | 43 | 32 | L |
| 11 | M | 19 | 60 | TBI | NSF | 7 | 20 | L |

TABLE 1-continued

Patient Clinical Demographics for Stereotactic Laser Amygdalohippocampotomy (SLAH) Series

| Sample# | Gender | Age (yrs) | BSF (sz/mo) | Etiology | Outcome | Duration (yrs) | Follow-up (mos) | Laterality |
|---|---|---|---|---|---|---|---|---|
| 12 | F | 62 | 2 | Inf | NSF | 61 | 12 | L |
| 13 | M | 32 | 2 | Unk | NSF | 25 | 14 | L |
| 14 | M | 26 | 1 | Unk | NSF | 19 | 22 | L |
| 15 | M | 45 | 4 | Unk | NSF | 37 | 25 | L |
| 16 | F | 58 | 2 | Unk | NSF | 37 | 13 | R |

Etiology = Etiology of epilepsy;
TBI = traumatic brain injury;
Unk = unknown;
CVA = stroke;
Abor = abortion;
Inf = infection;
Pre = preeclampsia;
Duration = duration of epilepsy prior to SLAH;
SF = seizure-free,
NSF = not seizure-free;
Laterality = laterality of SLAH,
L = left,
R = right;
SLAH = Selective Laser Amygdalohippocampotomy.
BSF = baseline seizure frequency The temporal lobe seizure focus was localized to the left hemisphere in 9 patients, and the right hemisphere in 7 patients. Median pre-operative, baseline seizure frequency was 2 seizures per month (range: 0.25 to 60 seizures per month), with a mean of $1.4 \pm 0.6$ and $8.7 \pm 6.4$ (mean±SEM) in the SF and NSF groups, respectively (t-test, two-tailed P value=0.341). Seizure duration before surgery averaged $19.1 \pm 6.0$ years and $30.3 \pm 5.8$ years for the SF and NSF groups, respectively (t-test, two-tailed P value=0.206). Post-operative SLAH seizure outcome was assessed at a mean follow-up of 18 months (range: 12 to 32 months), with a mean of $16.9 \pm 2.6$ and $18.3 \pm 2.3$ in the SF and NSF groups, respectively (t-test, two-tailed P value=0.678). There was no significant difference in pre-operative anticonvulsant medication use between patients in the post-operative seizure-free compared to the non-seizure-free groups (Table 2).

TABLE 2

Pre-operative Antiepileptic Medication Use of Patients for SLAH Series

| Medication | Use (Yes/No) | Seizure-Free Post-op | Not-Seizure-Free Post-op | pvalue[#] |
|---|---|---|---|---|
| Carbamazepine | Yes | 4 (25.0%) | 6 (37.5%) | 1.00 |
| | No | 3 (18.8%) | 3 (18.8%) | |
| Phenytoin | Yes | 4 (25.0%) | 5 (31.3%) | 1.00 |
| | No | 3 (18.8%) | 4 (25.0%) | |
| Valproic acid | Yes | 1 (6.2%) | 5 (31.3%) | 0.145 |
| | No | 6 (37.5%) | 4 (25.0%) | |
| Oxcarbazepine | Yes | 2 (12.5%) | 2 (12.5%) | 1.00 |
| | No | 5 (31.3%) | 7 (43.8%) | |
| Gabapentin | Yes | 0 (0.0%) | 2 (12.5%) | 0.475 |
| | No | 7 (43.8%) | 7 (43.8%) | |
| Topiramate | Yes | 4 (25.0%) | 1 (6.2%) | 0.106 |
| | No | 3 (18.8%) | 8 (50.0%) | |
| Phenobarbital | Yes | 1 (6.2%) | 4 (25.0%) | 0.308 |
| | No | 6 (37.5%) | 5 (31.3%) | |
| Zonisamide | Yes | 1 (6.2%) | 2 (12.5%) | 1.00 |
| | No | 6 (37.5%) | 7 (43.8%) | |
| Levetiracetam | Yes | 5 (31.3%) | 5 (31.3%) | 0.633 |
| | No | 2 (12.5%) | 4 (25.0%) | |
| Vigabatrin | Yes | 0 (0.0%) | 1 (6.2%) | 1.00 |
| | No | 7 (43.8%) | 8 (50.0%) | |
| Lacosamide | Yes | 1 (6.2%) | 0 (0.0%) | 0.438 |
| | No | 6 (37.5%) | 9 (56.2%) | |
| Lamotrigine | Yes | 5 (31.3%) | 4 (25.0%) | 0.358 |
| | No | 2 (12.5%) | 5 (31.3%) | |
| Other* | Yes | 6 (37.5%) | 7 (43.8%) | 1.00 |
| | No | 1 (6.2%) | 2 (12.5%) | |

*Other includes lorazepam, zomig, clonazpam, clobazam, primidone, fycoma, temazepam, mysoline, diazepam;
[#]Fisher exact test Demographic and seizure focus localization data for all patients undergoing SLAH demonstrated no significant differences for patient gender, age, baseline seizure frequency, ethnicity, MRI brain medial temporal sclerosis status, ictal surface or subdural/depth electrode EEG seizure focus localization concordance, PET scan concordance, and neuropsychological testing results between the seizure-free and non-seizure-free groups (Table 3).

TABLE 3

Demographic and Seizure Focus Localization Data of Patients for SLAH Series

| | | Seizure-free Post-op | Not-Seizure-free Post-op | p-value* |
|---|---|---|---|---|
| Gender | Male | 5 | 5 | 0.633 |
| | Female | 2 | 4 | |
| Age | Mean (SD) in years | 34.9 (13.3) | 43.0 (14.6) | 0.289[#] |

TABLE 3-continued

Demographic and Seizure Focus Localization Data of Patients for SLAH Series

|  |  | Seizure-free Post-op | Not-Seizure-free Post-op | p-value* |
|---|---|---|---|---|
| Seizure Frequency | >2 | 2 | 3 | 1.000 |
| (/month; median = 2) | ≤2 | 5 | 6 |  |
| Ethnicity | Caucasian | 3 | 4 | 1.000 |
|  | Hispanic/Other | 2 | 5 |  |
| MRI Results | MTS | 4 | 7 | 1.000 |
|  | Normal/other | 2 | 3 |  |
| PET Scan | Hypometabolism/Concordant | 6 | 6 | 0.229 |
|  | Disconcordant/Nonlocalizing | 0 | 3 |  |
| Ictal Scalp EEG | Temporal Lobe/Concordant | 5 | 10 | 0.375 |
|  | Nonlocalizing/Disconcordant | 1 | 0 |  |
| Ictal Subdural/Depth EEG | Temporal Lobe Concordant | 0 | 5 | 1.000 |
|  | Nonlocalizing/Disconcordant | 0 | 0 |  |
| Neuropsychological Testing | Lateralizing Concordant | 2 | 4 | 0.567 |
|  | Nonlateralizing/Disconcordant | 4 | 2 |  |

* Fisher Exact Test except where noted;
Mann-Whitney U Test, Z = 1.06.
Seizure Frequency = Baseline pre-operative seizure frequency.
Concordant/disconcordant = Concordance or disconcordance with temporal lobe treated with SLAH.
MTS = medial temporal sclerosis.

Figure 2:
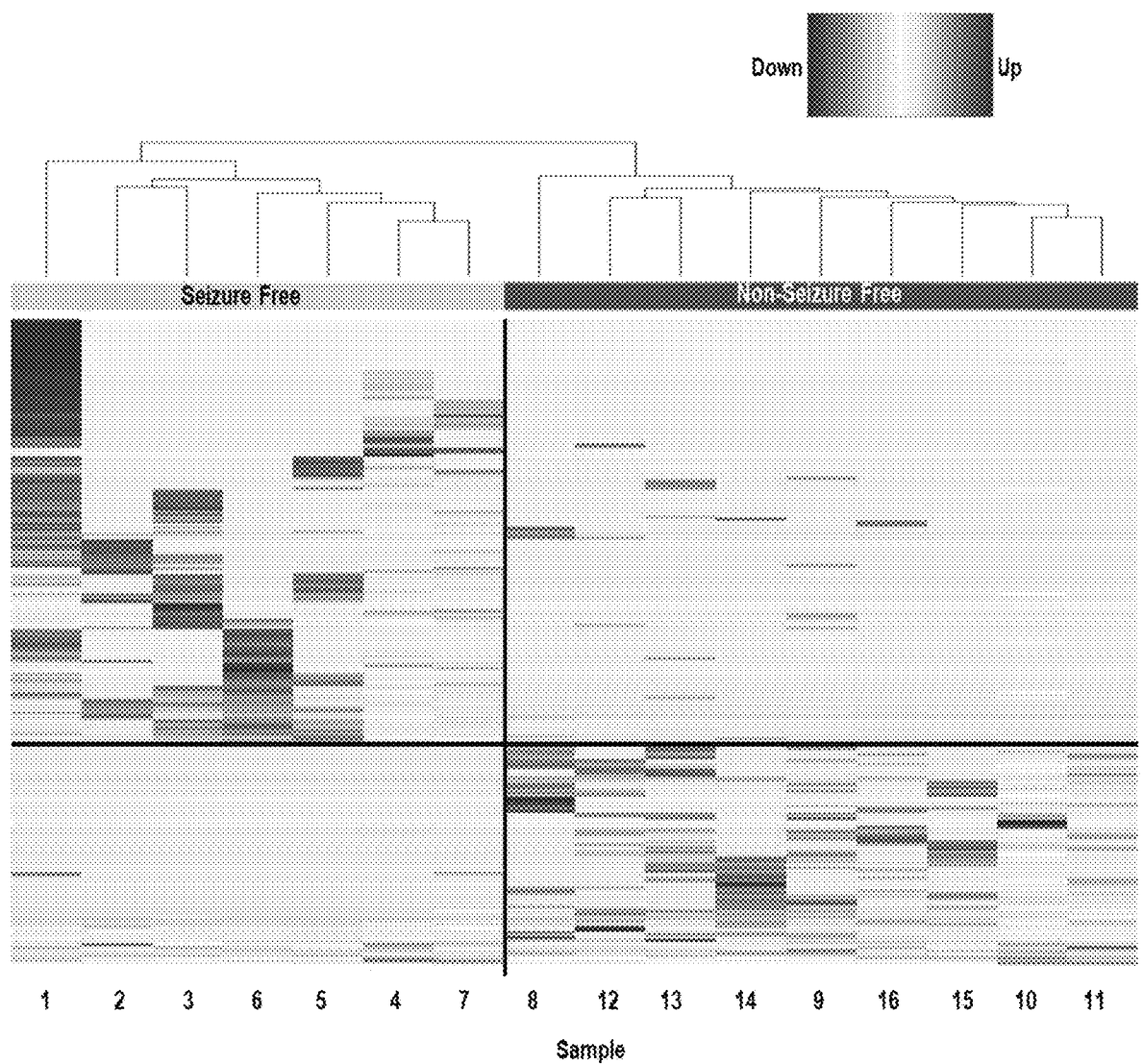
FIG. 2 depicts a heatmap generated in edgeR using the 250 most variable genes across samples. Unsupervised clustering showing the grouping of non-seizure free and seizure free patients. X-axis indicates sample ID from subject list in Table 1 (See Detailed Description). Red indicates a higher level of comparative expression while Blue indicates a lower level of expression.

MDS Plot and Heatmap Analysis. A multidimensional scaling plot (MDS) was generated using all annotated transcripts from each sample to look for segregation of outcome groups (FIG. 1). While one sample in the non-seizure free group was found to have a large biological coefficient of variation (BCV) distance from the remaining cluster of patients (sample #15), there was a general clustering and segregation of non-seizure free vs seizure-free outcome. Considering the variable nature of peripheral blood mononuclear cell (PBMC) expression patterns this result provided initial evidence of an outcome-predictive transcriptional profile. In an effort to reduce the general noise associated with PBMC expression, the top 250 most variable genes across samples were selected to generate a heatmap using the R package gplots (FIG. 2). This unsupervised analysis again showed a clustering of NSF vs SF patients with large sets of genes showing a pattern of increased expression in one patient group but not the other and vice versa (FIG. 2).

Figure 3:
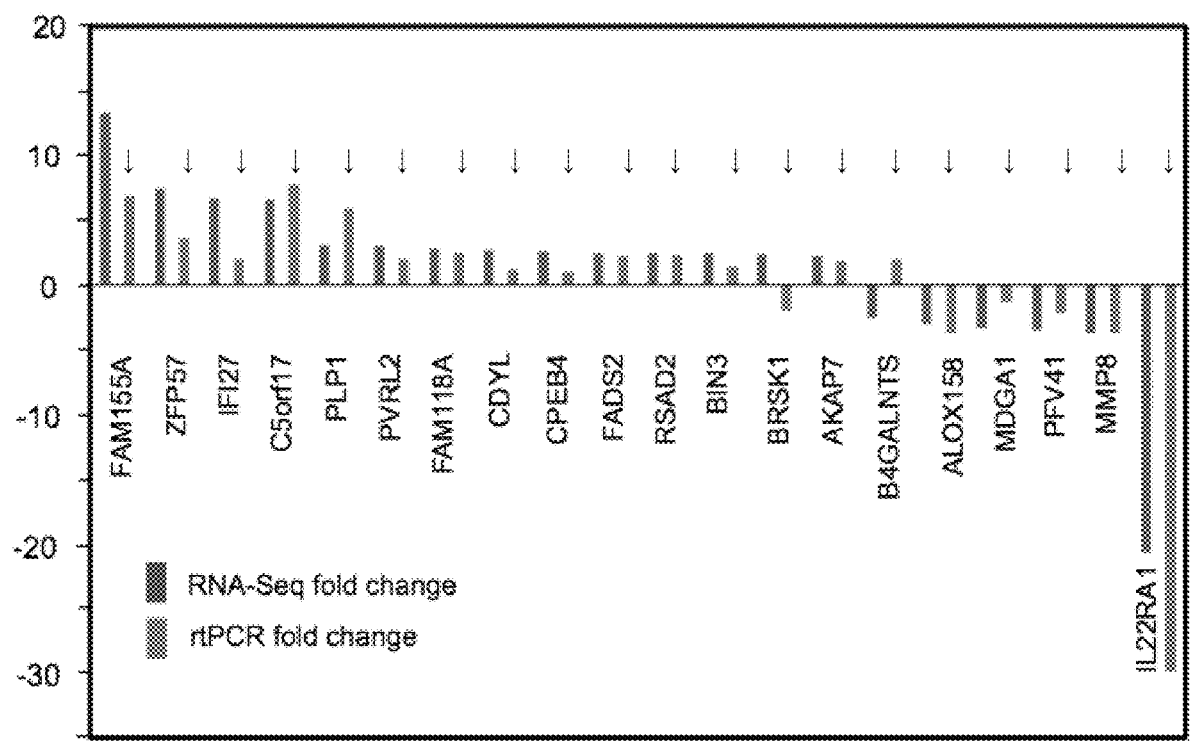
FIG. 3 depicts RNAseq vs rtPCR (each bar representing rtPCR being denoted by an arrow) fold expression validation run on all samples for all genes meeting the 2.0 FC, p-value <0.05, and FDR <0.05 cutoff criteria. rtPCR assays failed to generate product for ABCA4, GFAP, HBG1, BGN.

Differential Expression Analysis. Differential expression analysis was performed comparing the NSF (n=9) and SF (n=7) patient cohorts. Based on a cutoff of 2.0-fold change (p-value <0.05, FDR <0.05) 16 up-regulated genes and 8 down-regulated genes were identified (Table 4). Real time PCR (rtPCR) confirmation was performed on all samples for all genes meeting the differential expression cutoff criteria described above (FIG. 3). RtPCR assays for ABCA4, GFAP, HBG1 and BGN failed to amplify product while BRSK1 and B4GALNT3 generated results contradictory from the RNAseq values. The remaining 18 genes all showed confirmatory rtPCR results validating the RNAseq data in all samples.

TABLE 4

Pre-operative Leukocyte expression NSF vs SF Outcome Following SLAH, Fold Change > 2.0. SF = Seizure free, NSF = Non-Seizure free, FDR = False discovery rate, SLAH = stereotactic laser amygdalohippocampotomy. Fold-change expression relative to prognostic value for seizure-free outcome following SLAH.

| Up-Regulated | Fold-Change | FDR | p-Value | Down-Regulated | Change Fold- | FDR | p-Value |
|---|---|---|---|---|---|---|---|
| FAM155A | 13.4 | 1.3E-02 | 9.28E-06 | IL22RA1 | -20.7 | 2.0E-04 | 4.9E-08 |
| ABCA4 | 9.1 | 1.3E-02 | 1.00E-05 | BGN | -15.5 | 5.0E-03 | 2.3E-06 |
| ZFP57 | 7.4 | 5.8E-08 | 5.12E-12 | MMP8 | -4.6 | 1.0E-02 | 7.0E-06 |
| IFI27 | 6.7 | 3.3E-17 | 1.44E-21 | PF4V1 | -3.5 | 3.6E-02 | 3.4E-05 |
| C5orf17 | 6.7 | 4.5E-02 | 4.61E-05 | MDGA1 | -3.4 | 1.0E-04 | 1.8E-08 |
| PLP1 | 3.2 | 5.0E-03 | 5.77E-06 | ALOX15B | -3.1 | 9.0E-03 | 5.5E-06 |
| PVRL2 | 3.0 | 1.0E-03 | 9.03E-08 | HBG1 | -2.7 | 2.0E-03 | 1.5E-06 |
| FAM118A | 2.9 | 5.4E-05 | 1.44E-08 | B4GALNT3 | -2.5 | 4.5E-02 | 6.4E-05 |
| GFAP | 2.8 | 8.0E-03 | 8.66E-06 |  |  |  |  |
| CDYL | 2.7 | 2.0E-04 | 1.23E-07 |  |  |  |  |
| CPEB4 | 2.6 | 4.0E-04 | 2.16E-07 |  |  |  |  |
| FADS2 | 2.6 | 2.0E-03 | 1.63E-06 |  |  |  |  |

TABLE 4-continued

Pre-operative Leukocyte expression NSF vs SF Outcome Following SLAH,
Fold Change > 2.0. SF = Seizure free, NSF = Non-Seizure free, FDR = False discovery rate,
SLAH = stereotactic laser amygdalohippocampotomy. Fold-change expression relative to
prognostic value for seizure-free outcome following SLAH.

| Up-Regulated | Fold-Change | FDR | p-Value | Down-Regulated | Change Fold- | FDR | p-Value |
|---|---|---|---|---|---|---|---|
| RSAD2 | 2.5 | 1.0E−03 | 8.45E−07 | | | | |
| BIN3 | 2.5 | 1.0E−03 | 7.21E−07 | | | | |
| BRSK1 | 2.4 | 1.2E−03 | 1.44E−05 | | | | |
| AKAP7 | 1.8 | 3.4E−02 | 4.64E−05 | | | | |

SF = Seizure free,
NSF = Non-Seizure free,
FDR = False discovery rate,
SLAH = stereotactic laser amygdalohippocampotomy.

Pathway Analysis. The differentially expressed leukocyte genes were first compared with reference gene lists to identify significantly overrepresented molecular functions, biological processes and pathways [11]. This test produced one marginally statistically significant result, identifying a biological process that contained 4 of the 24 dysregulated genes in our data set (Panther overrepresentation test, p=0.048). The four genes, HBG1, FADS2, PLP1 and ALOX15B all play a role in long-chain fatty acid metabolism. We also used Ingenuity® Pathway Analysis (IPA®) to identify significantly associated biological pathways associated with seizure-free outcome. This analysis identified the following biological pathways in which clustering of these genes was significantly overexpressed: Cell morphology, lipid metabolism/molecular transport, inflammatory response/organismal injury and abnormality, and nervous system development/cellular development (Table 5).

TABLE 5

Biological Pathways Associated with Seizure Outcome Following SLAH (p < 0.001)*

| Categories | Genes |
|---|---|
| Cell Morphology | ABCA4, BGN, BIN3, BRSK1, CPEB4, FADS2, BRSK1, CPEB4, FADS2, GFAP, NECTIN2, PLP1, MMP8, ZFP57 |
| Lipid Metabolism, Molecular Transport, | ABCA4, FADS2, PLP1 |
| Inflammatory Response, Organismal Injury & Abnormalities | ABCA4, BGN, BIN3, FADS2, GFAP, IFI27, MMP8, PLP1 |
| Nervous System Development & Cellular Development | GFAP, PLP1 |

SLAH = stereotactic laser amygdalohippocampotomy.
*Ingenuity ® Pathway Analysis (IPA ®), Qiagen.

Figure 4:
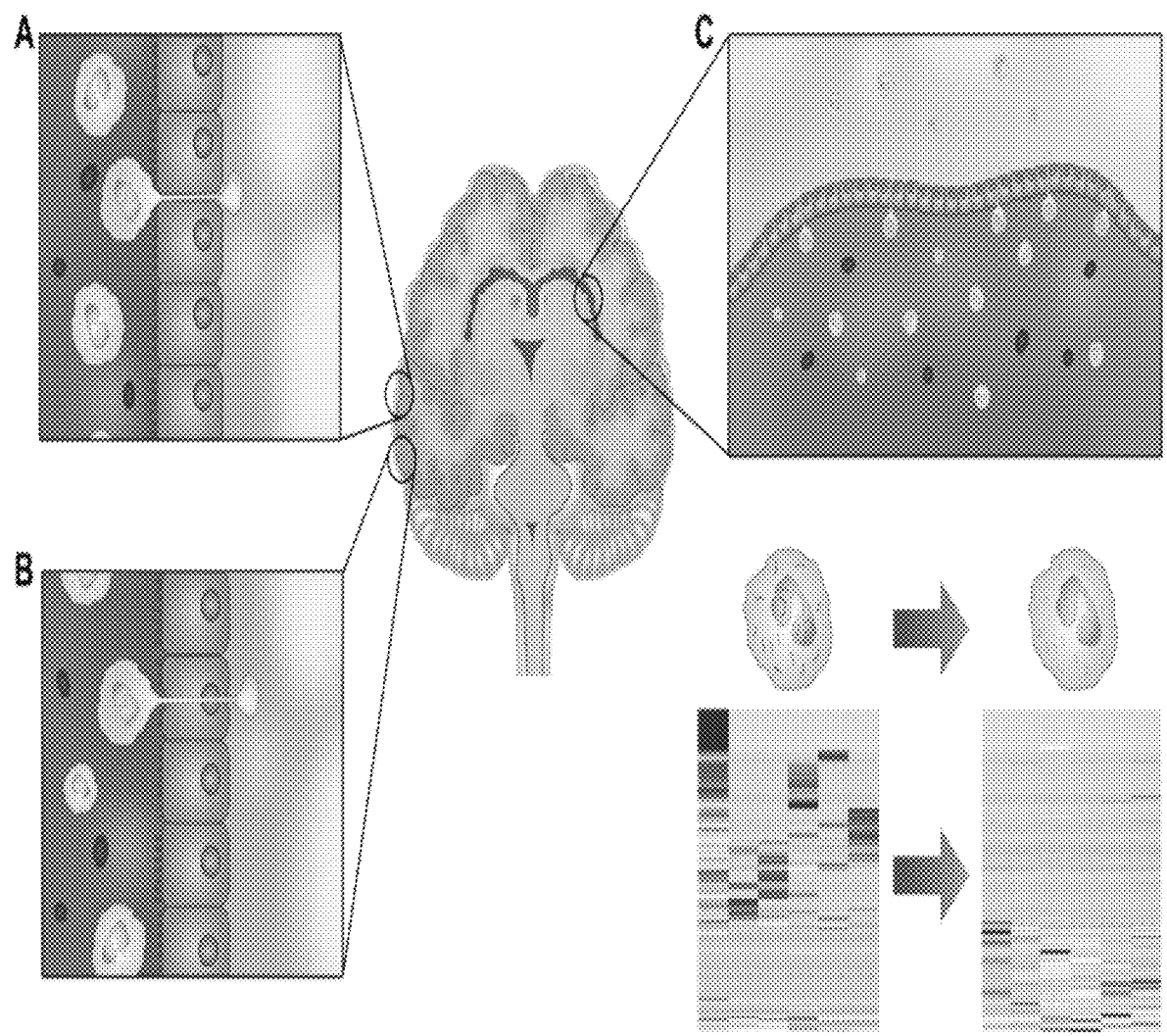
FIG. 4 depicts multiple mechanisms of leukocyte trafficking in the brain. Once in the brain the leukocyte RNA expression profile is altered by the cortical environment. This altered profile is maintained once the leukocyte returns to the peripheral blood. A. Human epileptic brain tissue possesses abnormal endothelial cell tight junctions with breach of the blood-brain barrier (BBB) permitting cerebral vascular endothelium intercellular leukocyte entry into the brain. B. With epilepsy-associated neuroinflammation, leukocyte trafficking across the BBB also occurs via cerebral vascular endothelial transcellular diapedesis. C. Choroid plexus vascular endothelium intercellular leukocyte entry into the cerebral spinal fluid. Leukocyte RNA transcription profile change from exposure to cerebral molecular microenvironment producing genomic transformation recapitulating temporal lobe epilepsy pathophysiology in peripheral blood leukocyte (bottom right).

RNA-Seq was employed to identify preoperative peripheral leukocyte gene expression profiles in TLE patients undergoing SLAH in order to test the hypothesis that these RNA expression profiles are prognostic for post-operative seizure-free outcome. We found that peripheral leukocyte RNA expression patterns differentiated patients with SF and NSF outcomes, with 24 transcripts differing by ≥2-fold between these patient groups. To fully explore the question of whether circulating leukocytes may express different gene expression profiles as a result of their presence in the blood streams of TLE patients with different proclivities for SF or NSF surgical outcomes, it is important to first examine the varied means by which immune cells are recruited and infiltrated into the epileptic brain (FIG. 4). Historically, the brain was considered an immunologically-privileged organ [12].

However, it is now known that the brain is immunologically active [13,14]. Experimental and clinical evidence supports the concept of a link between epilepsy and systemic and central nervous system inflammation, both of which impact seizure susceptibility [13,15]. Inflammation is significantly involved in the pathophysiology of epilepsy and inflammatory mediators are produced by neurons, astrocytes, and microglia [16]. With activated leukocytes being shown to infiltrate the brain in several forms of human epilepsy, as well as evidence for significant blood-brain barrier (BBB) disruption, there is opportunity for leukocyte communication with brain cells [16,17]. This communication between leukocytes and neuronal tissue can influence both epileptogenicity and seizure onset [16,18]. Human epileptic brain tissue also demonstrates abnormal endothelial cell tight junctions with breach of the BBB, thus allowing WBC infiltration of the perivascular spaces of the disrupted BBB [14,15] (FIG. 4).

In addition, during neuroinflammation, leukocyte trafficking across the BBB can also occur via transcellular diapedesis (FIG. 4). Seizure-produced BBB disruption also increases natural killer (NK) cell migration into brain tissue, which further contributes to cerebral inflammation in epileptic foci [20]. This immunopathogenesis of epilepsy involves reciprocal endothelial-leukocyte interactions in the context of BBB disruption [14]. Furthermore, the endothelial-immune cell bidirectional interactions that modulate leukocyte migration into the brain are coordinated by immunoglobulin endothelial cell adhesion molecules and leukocyte integrins [14]. All of the above-mentioned mechanisms of immune cell migration into the brain provide an immunosurveillance function under both normal conditions and during neuroinflammatory pathologies such as temporal lobe epilepsy [14].

Of the 24 differentially expressed genes in the leukocytes of TLE patients with SF versus NSF outcomes, four are associated with long-chain fatty acid metabolism: ALOX15B (FC: −3.1), FADS2 (FC: +2.6), PLP1 (FC: +3.2), and HGB1 (FC: −2.7). ALOX15B (arachidonate 15-lipoxygenase, type B) is an interesting candidate biomarker that is down-regulated in association with post-SLAH seizure-free outcome in leukocytes (Table 4). ALOX15B encodes a 15-lipoxygenase that oxidizes fatty acids to inflammation-promoting substances and is responsible for regulating IL-12 mediated chronic inflammation and inflammatory activity through IL-1β and TNF-α [22,23]. Biological membranes, which consist of phospholipids containing polyunsaturated fatty acids, are very susceptible to ROS oxidation, known as lipid peroxidation [24]. There is also evidence for an association between mitochondrial oxidative stress and dysfunction both as a result of seizures and as a contributor to epileptogenesis [24]. Down-regulation of ALOX15B may contribute to post-SLAH seizure freedom through an anti-inflammatory reduction of fatty acid oxidation, thus inhibiting epileptogenicity.

Further supporting this concept, it is widely known that metabolism-based therapy for medically-refractory epilepsy has included generation of fatty acid oxidation products known as ketone bodies. These ketone bodies serve as alternatives to glucose fuel for the brain in the high-fat, low carbohydrate and low-protein antiseizure ketogenic diet [25]. The ketogenic diet has been shown to decrease mitochondrial ROS, increase cellular antioxidant capacity, and prevent mtDNA deletions and cell death [24]. Ketone bodies possess neuroprotective activity, decrease reactive oxygen species (ROS), and increase cellular adenosine triphosphate (ATP) levels [25]. Evidence from a rodent model of temporal lobe epilepsy links ketone body suppression of epilepsy and cognition enhancement to the mitochondrial permeability transition (mPT) which regulates ROS and ATP levels and cell death pathways [25].

Additional confirmation of the role of lipid metabolism as a biomarker comes from the IPA analysis based on the same 24 significantly differentially expressed genes in the patient PBMCs associated with post-SLAH seizure-free outcome (Table 5), which also identified cell morphology, inflammation, and nervous system and cell development as key biological pathways associated with seizure outcome. The identification of these biological processes is particularly interesting as epileptogenesis involves activation of the central nervous and systemic immune systems, which in turn can be modulated by lipid metabolism pathways [26]. As mentioned above, PLP1 and FADS2 were up-regulated in association with post-SLAH seizure-free outcome while IPA identified a third gene involved in lipid metabolism and transport that was also significantly up-regulated (ABCA4 FC: +9.1) in our data set. ABCA4 uses ATP to transport a variety of different substrates including the phospholipids, phosphatidylcholine and phosphatidylethanolamine, across biological membranes [27,28]. Both phosphatidylcholine and phosphatidylethanolamine are significantly depleted by seizure activity [29]. ATP-binding cassette transporters are critical to the integrity of the central nervous system as key regulators of cellular lipid transport processes, thus maintaining membrane lipid symmetry [30,31]. Conversely, the loss of ABCA4 activity results in accumulation of lipid debris and defective phagosome processing [32]. The importance of maintaining potentially excitable membrane lipid symmetry is again underscored by the anti-epileptic effects of fatty acid nutritional supplementation. Although more studies are needed, clinical trial evidence currently suggests that supplementation with omega-3 fatty acids may decrease the frequency and duration of seizures and enhance quality of life in patients with epilepsy [26,33,34]. Given this evidence, the role of increased ABCA4 expression may likely prove protective against seizure activity.

Likewise, the up-regulation of both PLP1 and FADS2 also has some functional evidence mechanistically for improved outcome following SLAH. Synaptic transmission and neuronal excitability are regulated by myelination, and hippocampal demyelination has been detected in temporal lobe epilepsy [35]. PLP1 expression is known to counteract this loss of myelination and is able to prevent oligodendroglial cell loss [36,37]. Additionally, FADS2 is known to mediate direct fatty acid desaturation to yield docosahexaenoic acid (DHA) in human cells [38]. DHA is an omega-3 fatty acid that is highly abundant in neuronal membranes [39]. DHA is involved in synaptic membrane function and modulates glutamate availability by inhibiting its transporter, glutamate/aspartate transporter (GLAST) [40]. DHA also regulates GABA receptor subunits; raises the seizure threshold in mice and rats; prolongs seizure latency; reduces the amount of rescue-medication required during antiseizure therapy; reduces epileptic activity through frequency-dependent blockade of sodium channels; and has been shown in vitro to decrease hippocampal excitability through CA3 circuitry [39,40,41]. DHA anti-epileptic activity may also be involved though modulation of neurotransmitter receptors, ion channels and regulation of synaptic plasticity while also deceasing neuronal excitability and potentiating GABAergic activity [39,40]. Further evidence has been shown through systemically administered DHA which was able to inhibit kindling progression and electrically induced hippocampal hyperexcitability associated with evoked seizures, thus limiting progression of limbic seizures in a rodent model of temporal lobe epilepsy [40]. Higher levels of functional DHA mediated by FADS2 expression would again argue for a mechanistically protective effect for prospective patients. Additionally, the derivative of DHA resulting from seizures and phospholipase A2 activity, neuroprotectin 1 (NPD1), inhibits hippocampal evoked epileptiform activity and motor seizures [40]. It is also anti-inflammatory through down-regulation of proinflammatory cytokines and is protective against oxidative stress [40].

Taken together these results suggest that over-expression of leukocyte genes in biological pathways supporting lipid metabolism, function, and transport, as well as inhibition of genes regulating fatty acid oxidation are prognostic for post-SLAH seizure-free outcome. As lipid metabolism and transport are critical to normal central nervous system health and function, these findings of significant pathway associations fit with a mechanistic view of a seizure-free outcome. Specifically, up-regulation of ABCA4 and PLP1 may promote post-SLAH seizure freedom through maintenance of central nervous system membrane lipid symmetry and myelinated oligodendroglial cell populations, respectively. Down-regulation of ALOX15B and up-regulation of FADS2 may further support post-SLAH seizure-free outcome through reduction of inflammatory fatty acid oxidation and enhancement of DHA anti-epileptic activity, respectively.

In conclusion, next-generation sequencing and differential expression analyses performed in 16 consecutive patients with intractable temporal lobe epilepsy demonstrate leukocyte-RNA expression patterns predictive of seizure-free outcome following SLAH. The results support that a profile of leukocyte gene expression is prognostic for seizure-free outcome following SLAH. This could have the effect of improving the selection of candidates for SLAH, and support further development of the concept of "neurosurgical genomics" by which pre-operative leukocyte gene expression may predict the desired response to neurosurgical operative intervention.

Methods

Patient Population. This study involves a consecutive series of 16 patients evaluated at the Arizona Comprehensive Epilepsy Program at Banner University Medical Center—Tucson for intractable temporal lobe epilepsy. All patients met the Task Force of the ILAE (International League Against Epilepsy) Commission on Therapeutic Strategies definition of drug-resistant epilepsy. Therefore, each patient had "intractable epilepsy" resistant to at least two well tolerated, appropriately chosen and prescribed anti-epileptic drug regimens either as mono-therapies or in combination [10,42]. This study was approved by and conducted in accordance with the approved protocols and subject consent forms provided by the University of Arizona College of Medicine Institutional Review Board. Informed consent was obtained from all participants in the study.

Figure 5:
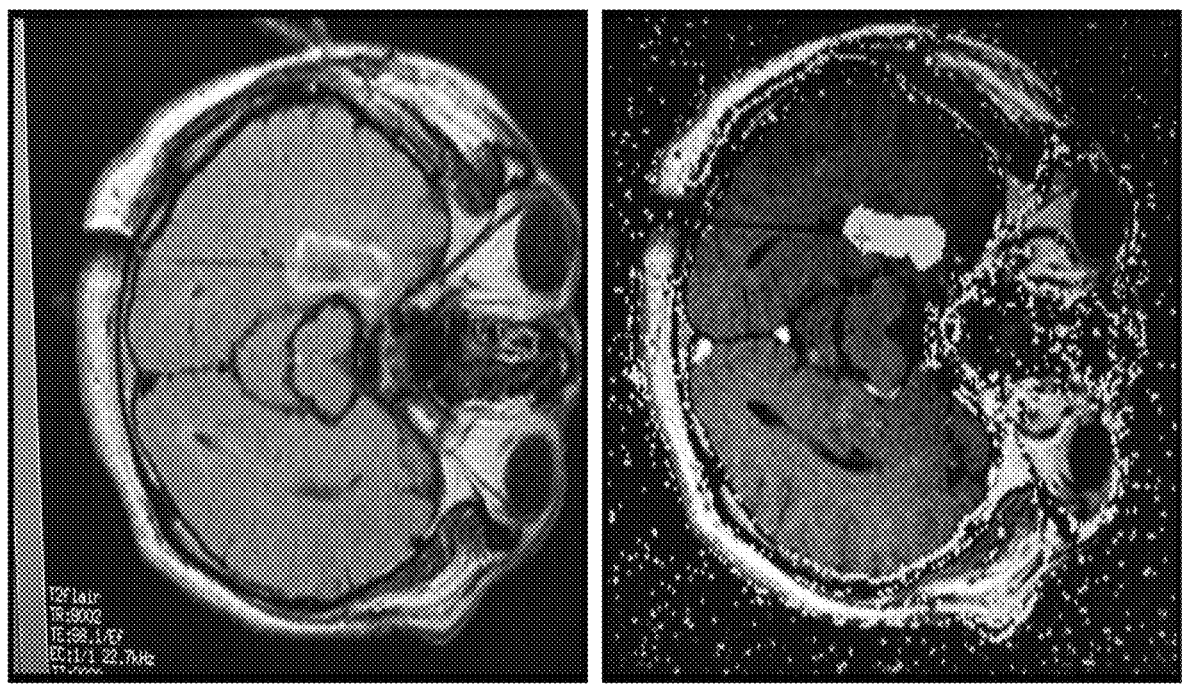
FIG. 5 depicts real time T2-FLAIR (left) and thermal (right) MRI brain images of immediate post-operative brain demonstrating blood brain barrier disruption outline and of permanent brain tissue destruction during stereotactic laser amygdalohippocampotomy (SLAH) (orange).

Seizure Focus Localization. All 16 patients underwent Phase I and, where appropriate, Phase II evaluation for epilepsy surgery candidacy as previously described [4] (FIG. 5). Phase I evaluation may include long-term surface ictal EEG recording, MRI brain scanning, PET brain scanning and neuropsychological testing. For patients in whom Phase I long-term scalp-EEG recording failed to localize the ictal seizure focus, Phase II evaluation included long-term subdural and/or depth EEG recording. In all patients, the ictal seizure focus was localized to a single temporal lobe.

Seizure Focus Ablation and Seizure Outcome. In all 16 patients, based on seizure focus localization, SLAH was performed as previously described [43]. The neurosurgical operative technique for SLAH involves stereotactic planning of an occipital to amygdalohippocampal trajectory for MRI-thermal guided laser ablation AH employing between 3 to 5 thermal ablation isocenters per patient. The goal is optimal thermal ablation of the amygdala and hippocampus, from the amygdala anteriorly to the hippocampus at least at the level of the tectum posteriorly. All patients were evaluated at a minimum of 12-months follow-up on anticonvulsant medication to determine post-operative seizure outcome defined as "seizure-free" or "not seizure-free" (Table 1). Patients experiencing "auras only" were classified as "not seizure-free". A patient having a rare seizure due to anticonvulsant medication non-compliance followed by prolonged resumption of seizure freedom associated with anticonvulsant medication compliance was classified as "seizure-free".

Leukocyte RNA Acquisition and Expression. Pre-operative whole blood was obtained immediately prior to placement of the stereotactic head frame before SLAH and was stored in RNA stabilization Solution (Qiagen, Valencia, CA) at −80° C. until RNA extraction was performed. Total RNA was extracted from leukocytes using RNeasy lipid tissue mini kit (Qiagen, Valencia, CA) following manufacturer's instructions. First-strand cDNA was prepared with the SuperScript III kit (Life Technologies/Thermo Fisher Scientific, Carlsbad, CA). RNA Samples were assessed for quality with a High Sensitivity RNA Analysis Kit (Fragment Analyzer; Advanced Analytical Technologies, Ankeny, IA). Concentration was determined using a Quant-iT RiboGreen RNA Assay Kit (Molecular Probes; Thermo Fisher Scientific, Carlsbad, CA). RNASequence (RNASeq) Libraries were constructed using a stranded mRNA-Seq Kit (TDS KR0960-v3.15; KapaBiosystems, Wilmington, MA). After completion, quality and average fragment size were assessed with the Fragment Analyzer (Advanced Analytical Technologies, Ankeny, IA). Concentration was determined with the Illumina Universal Adaptor-specific qPCR kit (KapaBiosystems, Wilmington, MA). Equimolar samples were pooled and clustered for sequencing on the HiSeq2500 (Illumina, San Diego, CA). Sequencing was performed using Rapid-Run SBS 2×100 bp chemistry (Illumina, San Diego, CA) as previously described [44].

Sequence analysis. Sample data were demultiplexed, trimmed and quality filtered using Trimmomatic (USADelLab, Aachen, Germany). Fastq files were splice aligned against the GRCh37 reference genome using STAR aligner version 2.5.2b [45]. Gene expression counts were obtained using htseq-count version 0.6.1 [46]. Both splice alignment and counting were performed with Ensembl Annotation of the NCBI reference genome and raw counts analyzed with edgeR version 3.16.5 [47].

Differential expression analysis. Differential expression was analyzed in edgeR, version 3.16.5, in R edgeR's exactTest function. Gene expression counts were first normalized using the calcNormFactors function, which uses the trimmed mean of M values (TMM) to create a set of scaling factors that eliminates composition biases between sample libraries. Due to the variance between samples, the trended dispersion (the dispersion calculated from a gene's abundance) was used for the exactTest calculation.

Quantitative reverse transcriptase polymerase chain reaction (qRT-PCR). RNA from peripheral blood was isolated for each patient using the PAXgene blood RNA kit (Qiagen, Hilden, Germany) and cDNA was generated with the SuperScript III kit (Life Technologies/Thermo Fisher Scientific, Carlsbad, CA). Taqman probes were obtained from Life Technologies for the genes as validated using control cDNAs. Taqman reactions were performed in triplicate in a 15 uL reaction volume using the Taqman Fast Advance Master Mix (Thermo Fisher Scientific, Carlsbad, CA). All reactions were run on an ABI 7900HT using the SDS 2.4 software (Life Technologies/Thermo Fisher Scientific, Carlsbad, CA) with ABI384 well Optical PCR plates and AB-1170 Optical PCR film (Fisher Scientific International, Inc., Hampton, NH). All samples were run with the endogenous control GAPDH probe set (Life Technologies/Thermo Fisher Scientific, Carlsbad, CA). Differential expression analysis was performed using the standard delta-delta CT method [48].

Pathway and enrichment analysis. Differentially expressed transcripts were analyzed for enrichment of GO terms using the Overrepresentation Test (release 13.1) [11], accessing the GO Ontology database. Molecular process, cellular component and biologic process annotation databases were also used. Ingenuity® Pathway Analysis (IPA®) of all differentially expressed leukocyte genes predictive of seizure-free outcome was performed to further identify biological pathways (categories) involving diseases and functional annotations in which clustering of seizure outcome associated genes were significantly over expressed (Qiagen, Hilden, Germany).

Feature selection. RNA-seq has some major advantages over microarrays such as providing less noisy data and detecting novel transcripts and isoforms. The first property can improve the predictive performance of classification algorithms, while the second may reveal biomarkers that are tissue specific or that were previously not known to exist. The objective is to find a predictive model that uses expression data from a set of genes that show significantly different expression patterns (features) to calculate a score that correlates with how likely a person with a particular profile is to have a seizure-free outcome after SLAH. Our learning approach addresses some of the challenges that come from large-scale genomic datasets. Whole transcriptome (RNA-Seq) data were analyzed for prognostic value for seizure-free outcome following SLAH. We utilized multivariate logistic regression as our model of gene expression associated with seizure-free post-surgery outcome. The receiver-operating characteristic assessed the quality of our classification. The important features formed the basis for assessing the most informative markers for blood testing. We present a prioritized subset of genes and prognostic models to aid neurophysiologists, epileptologists, and epilepsy surgeons in understanding the molecular mechanisms of temporal lobe epilepsy, to develop better potentially predicitive models for selection of SLAH candidates, and to possibly improve post-surgical seizure outcome.

While the preferred embodiments of the present technology have been illustrated in detail, it should be apparent that modifications and adaptations to those embodiments may occur to one skilled in the art without departing from the scope of the present technology.

REFERENCES

1. Schachter S C. Seizure disorders. Med Clin North Am. 2009 March; 93(2):343-51, viii. doi: 10.1016/j.mcna.2008.10.001.
2. Brodie M J. Diagnosing and predicting refractory epilepsy. Acta Neurol Scand Suppl. 2005; 181:36-9. doi: 10.1111/j.1600-0404.2005.00507.x
3. Asadi-Pooya A A, Rostami C. History of surgery for temporal lobe epilepsy. Epilepsy Behav. 2017 May; 70 (Pt A):57-60. doi: 10.1016/j.yebeh.2017.02.020. Epub 2017 Apr. 12.
4. Weinand M E, Wyler A R, Richey E T, Phillips B B, Somes G W. Long-term ictal monitoring with subdural strip electrodes: prognostic factors for selecting temporal lobectomy candidates. J Neurosurg. 1992 July; 77(1):20-8. doi: 10.3171/jns.1992.77.1.0020
5. Gross R E, Willie J T, Drane D L. The Role of Stereotactic Laser Amygdalohippocampotomy in Mesial Temporal Lobe Epilepsy. Neurosurg Clin N Am. 2016 January; 27(1):37-50. doi: 10.1016/j.nec.2015.08.004. Epub 2015 Oct. 24.
6. Kwon C S, Neal J, Telléz-Zenteno J, Metcalfe A, Fitzgerald K, Hernandez-Ronquillo L, Hader W, Wiebe S, Jetté N; CASES Investigators. Respective focal epilepsy surgery—Has selection of candidates changed? A systematic review. Epilepsy Res. 2016 May; 122:37-43. doi: 10.1016/j.eplepsyres.2016.02.007. Epub 2016 Feb. 12.
7. Mansouri A, Fallah A, Valiante T A. Determining surgical candidacy in temporal lobe epilepsy. Epilepsy Res Treat. 2012; 2012:706917. doi: 10.1155/2012/706917. Epub 2012 Feb. 21.
8. McCallum A P, Gallek M J, Ramey W, Manziello A, Witte M H, Bernas M J, Labiner D M, Weinand M E. Cortical gene expression correlates of temporal lobe epileptogenicity. Pathophysiology. 2016 September; 23(3):181-90. doi: 10.1016/j.pathophys.2016.05.006. Epub 2016 May 28.
9. Bina R W, Sprissler R, Walter C M, Labiner D, Hammer M, Weinand M. Hippocampal RNA Expression Varies According to Seizure Outcome and Seizure Frequency following Anterior Temporal Lobectomy with Amgydalo-hippocampectomy, Scientific Session III: Stereotactic and Functional Surgery, AANS Annual Meeting, Los Angeles, C A, Apr. 24, 2017.
10. Gallek M J, Skoch J, Ansay T, Behbahani M, Mount D, Manziello D, Witte M, Bernas M, Labiner D M, Weinand M E, Cortical gene expression: prognostic value for seizure outcome following temporal lobectomy and amygdalohippocampectomy. Neurogenetics 17(4):211-218 (2016).
11. Mi H, Muruganujan A, Casagrande J T, Thomas P D. Large-scale gene function analysis with the PANTHER classification system. Nature Protocols 8:1551-1566 (2013).
12. Xiao Z, Peng J, Yang L, Kong H, Yin F. Interleukin-1β plays a role in the pathogenesis of mesial temporal lobe epilepsy through the PI3K/Akt/mTOR signaling pathway in hippocampal neurons. J Neuroimmunol. 2015 May 15; 282:110-7. doi: 10.1016/j.jneuroim.2015.04.003. Epub 2015 Apr. 2.
13. Cerri C, Caleo M, Bozzi Y. Chemokines as new inflammatory players in the pathogenesis of epilepsy. Epilepsy Res. 2017 October; 136:77-83. doi: 10.1016/j.eplepsyres.2017.07.016. Epub 2017 Jul. 27.
14. Legido A, Katsetos C D. Experimental studies in epilepsy: immunologic and inflammatory mechanisms. Semin Pediatr Neurol. 2014 September; 21(3):197-206. doi: 10.1016/j.spen.2014.10.001. Epub 2014 Oct. 13.
15. Bauer J, Becker A J, Elyaman W, Peltola J, Rüegg S, Titulaer M J, Varley J A, Beghi E. Innate and adaptive immunity in human epilepsies. Epilepsia. 2017 July; 58 Suppl 3:57-68. doi: 10.1111/epi. 13784.
16. Wang H, Liu S, Tang Z, Liu J, Some cross-talks between immune cells and epilepsy should not be forgotten. Neurol Sci. 35(12):1843-9 (2014).
17. Fiala M, Avagyan H, Merino J J, Bernas M, Valdivia J, Espinosa-Jeffrey A, Witte M, Weinand M. Chemotactic and mitogenic stimuli of neuronal apoptosis in patients with medically in-tractable temporal lobe epilepsy. Pathophysiology. 2013 February; 20(1):59-69. doi: 10.1016/j.pathophys.2012.02.003. Epub 2012 Mar. 22.
18. Terrone G, Salamone A, Vezzani A. Inflammation and Epilepsy: preclinical findings and potential clinical translation. Curr Pharm Des. 2017 Sep. 25. doi: 10.2174/1381612823666170926113754. [Epub ahead of print]
19. Carman C V. Mechanisms for transcellular diapedesis: probing and pathfinding by 'invadosome-like protrusions'. J Cell Sci. 2009 Sep. 1; 122 (Pt 17):3025-35. doi: 10.1242/jcs.047522.
20. Bauer, S., Köller, M., Cepok, S., et al., 2008. N K and CD4+ T cell changes in blood after seizures in temporal lobe epilepsy. Exp. Neurol. 211, 370-377. doi: 10.1016/j.expneurol.2008.01.017
21. Magnusson L U, Lundqvist A, Karlsson M N, Skålen K, Levin M, Wiklund O, Borén J, Hultén L M. Arachidonate 15-lipoxygenase type B knockdown leads to reduced lipid accumulation and inflammation in atherosclerosis. PLOS One. 2012; 7 (8):e43142. doi: 10.1371/journal.pone.0043142. Epub 2012 Aug. 17.
22. Middleton M K, Rubinstein T, Pure E. Cellular and molecular mechanisms of the selective regulation of IL-12 production by 12/15-lipoxygenase. J Immunol. 2006 Jan. 1; 176(1):265-74.
23. Wu M Y, Lin T H, Chiu Y C, Liou H C, Yang R S, Fu W M. Involvement of 15-lipoxygenase in the inflammatory arthritis. J Cell Biochem. 2012 July; 113(7):2279-89. doi: 10.1002/jcb.24098.

24. Waldbaum S, Patel M. Mitochondria, oxidative stress, and temporal lobe epilepsy. Epilepsy Res. 2010 January; 88(1):23-45. doi: 10.1016/j.eplepsyres.2009.09.020. Epub 2009 Oct. 21.
25. Kim D Y, Simeone K A, Simeone T A, Pandya J D, Wilke J C, Ahn Y, Geddes J W, Sullivan P G, Rho J M. Ketone bodies mediate antiseizure effects through mitochondrial permeability transition. Ann Neurol. 2015 July; 78(1):77-87. doi: 10.1002/ana.24424. Epub 2015 May 6.
26. Gouveia T L, Vieira de Sousa P V, de Almeida S S, Nejm M B, Vieira de Brito J M, Cysneiros R M, de Brito M V, Salu B R, Oliva M L, Scorza F A, Naffah-Mazzacoratti Mda G. High serum levels of proinflammatory markers during epileptogenesis. Can omega-3 fatty acid administration reduce this process? Epilepsy Behav. 2015 October; 51:300-5. doi: 10.1016/j.yebeh.2015.07.021. Epub 2015 Aug. 25.
27. Ellinger P, Kluth M, Stindt J, Smits S H, Schmitt L. Detergent screening and purification of the human liver ABC transporters BSEP (ABCB11) and MDR3 (ABCB4) expressed in the yeast *Pichia pastoris*. PLOS One. 2013 Apr. 4; 8(4):e60620. doi: 10.1371/journal.pone.0060620. Print 2013.
28. Quazi F, Molday R S. Differential phospholipid substrates and directional transport by ATP-binding cassette proteins ABCA1, ABCA7, and ABCA4 and disease-causing mutants. J Biol Chem. 2013 Nov. 29; 288(48): 34414-26. doi: 10.1074/jbc.M113.508812. Epub 2013 Oct. 4.
29. de Freitas R M, do Nascimento K G, Ferreira P M, Jordán J. Neurochemical changes on oxidative stress in rat hippocampus during acute phase of pilocarpine-induced seizures. Pharmacol Biochem Behav. 2010 January; 94(3):341-5. doi: 10.1016/j.pbb.2009.09.015. Epub 2009 Oct. 1.
30. Piehler A P, Ozcürümez M, Kaminski W E. A-Subclass ATP-Binding Cassette Proteins in Brain Lipid Homeostasis and Neurodegeneration. Front Psychiatry. 2012 Mar. 5; 3:17. doi: 10.3389/fpsyt.2012.00017. eCollection 2012.
31. Quazi F, Molday R S. Lipid transport by mammalian ABC proteins. Essays Biochem. 2011 Sep. 7; 50(1):265-90. doi: 10.1042/bse0500265.
32. Reyes-Reveles J, Dhingra A, Alexander D, Bragin A, Philp N J, Boesze-Battaglia K. Phagocytosis-dependent ketogenesis in retinal pigment epithelium. J Biol Chem. 2017 May 12; 292(19):8038-8047. doi: 10.1074/jbc.M116.770784. Epub 2017 Mar. 16.
33. DeGiorgio C M, Taha A Y. Omega-3 fatty acids (@-3 fatty acids) in epilepsy: animal models and human clinical trials. Expert Rev Neurother. 2016 October; 16(10):1141-5. doi: 10.1080/14737175.2016.1226135. Epub 2016 Sep. 6.
34. Sarmento Vasconcelos V, Macedo C R, de Souza Pedrosa A, Pereira Gomes Morais E, Porfirio G J, Torloni M R. Polyunsaturated fatty acid supplementation for drug-resistant epilepsy. Cochrane Database Syst Rev. 2016 Aug. 17; (8):CD011014. doi: 10.1002/14651858.CD011014.pub2.
35. Gardner A, Jukkola P, Gu C. Myelination of rodent hippocampal neurons in culture. Nat Protoc. 2012 October; 7(10): 1774-82. doi: 10.1038/nprot.2012.100. Epub 2012 Sep. 6.
36. Osorio M J, Rowitch D H, Tesar P, Wernig M, Windrem M, Goldman S A. Concise Review: Stem Cell-Based Treatment of Pelizaeus-Merzbacher Disease. Stem Cells. 2017 February; 35(2):311-315. doi: 10.1002/stem.2530. Epub 2016 Nov. 23.
37. Marteyn A, Baron-Van Evercooren A. Is involvement of inflammation underestimated in Pelizaeus-Merzbacher disease? J Neurosci Res. 2016 December; 94(12):1572-1578. doi: 10.1002/jnr.23931. Epub 2016 Sep. 23.
38. Park H G, Park W J, Kothapalli K S, Brenna J T. The fatty acid desaturase 2 (FADS2) gene product catalyzes 44 desaturation to yield n-3 docosahexaenoic acid and n-6 docosapentaenoic acid in human cells. FASEB J. 2015 September; 29(9):3911-9. doi: 10.1096/fj. 15-271783. Epub 2015 Jun. 11.
39. Taha A Y, Zahid T, Epps T, Trepanier M O, Burnham W M, Bazinet R P, Zhang L. Selective reduction of excitatory hippocampal sharp waves by docosahexaenoic acid and its methyl ester analog ex-vivo. Brain Res. 2013 Nov. 6; 1537:9-17. doi: 10.1016/j.brainres.2013.09.004. Epub 2013 Sep. 13.
40. Musto A E, Gjorstrup P, Bazan N G. The omega-3 fatty acid-derived neuroprotectin D1 limits hippocampal hyperexcitability and seizure susceptibility in kindling epileptogenesis. Epilepsia. 2011 September; 52(9):1601-8. doi: 10.1111/j.1528-1167.2011.03081.x. Epub 2011 May 13.
41. Young C, Gean P W, Chiou L C, Shen Y Z. Docosahexaenoic acid inhibits synaptic transmission and epileptiform activity in the rat hippocampus. Synapse. 2000 August; 37(2):90-4.
42. Kwan P, Arzimanoglou A, Berg A T, Brodie M J, Hauser A W, Mathern G, Moshé S L, Perucca E, Wiebe S, French J. Definition of drug resistant epilepsy: consensus proposal by the ad hoc Task Force of the ILAE Commission on Therapeutic Strategies, Epilepsia, 51 (2010) 1069-1077.
43. Wicks R T, Jermakowicz W J, Jagid J R, Couture D E, Willie J T, Laxton A W, Gross R E. Laser Interstitial Thermal Therapy for Mesial Temporal Lobe Epilepsy. Laser Interstitial Thermal Therapy for Mesial Temporal Lobe Epilepsy. Neurosurgery. 2016 December; 79 Suppl 1:S83-S91. doi: 10.1227/NEU.0000000000001439
44. Wagnon J L, Korn M J, Parent R, Tarpey T A, Jones J M, Hammer M F, Murphy G G, Parent J M, Meisler M H. Convulsive seizures and SUDEP in a mouse model of SCN8A epileptic encephalopathy. Hum Mol Genet. 2015 Jan. 15; 24(2):506-15. doi: 10.1093/hmg/ddu470. Epub 2014 Sep. 16. PMID: 25227913
45. Dobin A, Davis C A, Schlesinger F, Drenkow J, Zaleski C, Jha S, Batut P, Chaisson M, Gingeras T R. STAR: ultrafast universal RNA-seq aligner. Bioinformatics. 2013 Jan. 1; 29(1):15-21. doi: 10.1093/bioinformatics/bts635. Epub 2012 Oct. 25.
46. Anders S, Pyl P T, Huber W. HTSeq—a Python framework to work with high-throughput sequencing data. Bioinformatics. 2015 Jan. 15; 31(2):166-9. doi: 10.1093/bioinformatics/btu638. Epub 2014 Sep. 25.
47. Robinson M D, McCarthy D J, Smyth G K. edgeR: a Bioconductor package for differential expression analysis of digital gene expression data. Bioinformatics. 2010 Jan. 1; 26(1):139-40. doi: 10.1093/bioinformatics/btp616. Epub 2009 Nov. 11.
48. Livak K J, Schmittgen T D. Analysis of relative gene expression data using real-time quantitative PCR and the 2(-Delta Delta C(T)) Method. Methods. 2001 December; 25(4):402-8. doi: 10.1006/meth.2001.1262.

What is claimed is:

1. A method of treating a subject with intractable epilepsy, comprising the steps of:
   a) obtaining RNA from leukocytes from the subject;
   b) based on the RNA present in the leukocytes, determining an expression level of 24 genes consisting of: FAM155A, ABCA4, ZFP57, IFI27, C5orf17, PLP1, PVRL2, FAM118A, GFAP, CDYL, CPEB4, FADS2, RSAD2, BIN3, BRSK1, AKAP7, IL22RA1, BGN, MMP8, PF4VI, MDGA1, ALOX15B, HBG1, and B4GALNT3;
   c) comparing the determined expression level with a control expression level for each gene;
   d) detecting upregulation of FAM155A, ABCA4, ZFP57, IFI27, C5orf17, PLP1, PVRL2, FAM118A, GFAP, CDYL, CPEB4, FADS2, RSAD2, BIN3, BRSK1, and AKAP7, and detecting downregulation of IL22RA1, BGN, MMP8, PF4VI, MDGA1, ALOX15B, HBG1, and B4GALNT3 relative to the control expression level for each gene; and
   e) treating the subject with ablation treatment.

2. The method of claim 1, wherein step c) comprises one or more of quantitative real time polymerase chain reaction (PCR) and digital droplet PCR.

3. The method of claim 1, wherein said ablation treatment comprises stereotactic laser amygdalohippocampotomy (SLAH) ablation of the amygdala and the hippocampus, from the amygdala anteriorly to the hippocampus at least at a level of the tectum posteriorly.

4. The method of claim 1, wherein said ablation treatment comprises an MRI-guided focused ultrasound or a focused ultrasound-based intervention.

\* \* \* \* \*

UNITED STATES PATENT AND TRADEMARK OFFICE
CERTIFICATE OF CORRECTION

| | |
|---|---|
| PATENT NO. | : 12,006,549 B2 |
| APPLICATION NO. | : 17/269092 |
| DATED | : June 11, 2024 |
| INVENTOR(S) | : Martin E. Weinand et al. |

It is certified that error appears in the above-identified patent and that said Letters Patent is hereby corrected as shown below:

In the Specification

Column 1, Lines 16-17, "applications the entirety of which is hereby incorporated herein by reference in its entirety herein" should be --applications is incorporated herein by reference in its entirety--.

Column 10, Lines 55-56, "diapedesis (FIG. 4)" should be --diapedesis [19] (FIG. 4)--.

Column 11, Line 13, "substance and" should be --substances [21] and--.

Signed and Sealed this
Twentieth Day of August, 2024

Katherine Kelly Vidal
*Director of the United States Patent and Trademark Office*